United States Patent
McNeal et al.

[11] Patent Number: 5,853,600
[45] Date of Patent: Dec. 29, 1998

[54] AXIAL SPIN BLOOD SEPARATION SYSTEM AND METHOD

[75] Inventors: Jack D. McNeal, Long Beach; Michael L. Bell, Fullerton, both of Calif.

[73] Assignee: Beckman Instruments, Inc., Fullerton, Calif.

[21] Appl. No.: 933,989

[22] Filed: Sep. 19, 1997

Related U.S. Application Data

[63] Continuation of Ser. No. 538,309, Oct. 3, 1995, abandoned.

[51] Int. Cl.$^6$ .................................................. B01D 21/26
[52] U.S. Cl. ........................ 210/789; 210/514; 210/515; 210/516; 210/518; 210/782; 210/787; 422/102; 436/177
[58] Field of Search ................................... 210/514, 515, 210/516, 518, 782, 787, 789; 422/102, 104; 436/177; 435/2

[56] References Cited

U.S. PATENT DOCUMENTS

| | | |
|---|---|---|
| 3,852,194 | 12/1974 | Zine, Jr. . |
| 3,918,920 | 11/1975 | Barber .................................... 422/104 |
| 3,981,804 | 9/1976 | Gigliello .................................. 210/516 |
| 4,197,287 | 4/1980 | Piasio et al. ............................ 422/102 |
| 4,350,593 | 9/1982 | Kessler ................................... 210/516 |
| 4,386,003 | 5/1983 | Fiehler ..................................... 252/60 |
| 4,762,798 | 8/1988 | Deutsch .................................. 422/102 |
| 4,846,974 | 7/1989 | Kelley et al. ........................ 210/380.1 |
| 4,861,477 | 8/1989 | Kimura .................................... 210/359 |
| 4,865,813 | 9/1989 | Leon ....................................... 422/102 |
| 4,981,585 | 1/1991 | Kelley et al. ........................... 210/138 |
| 5,030,341 | 7/1991 | McEwen et al. ......................... 210/94 |
| 5,236,604 | 8/1993 | Fiehler ................................... 210/782 |
| 5,266,199 | 11/1993 | Tsukagoshi et al. ................... 210/516 |
| 5,271,852 | 12/1993 | Luoma, II ............................... 210/789 |
| 5,275,731 | 1/1994 | Jahn ....................................... 210/518 |
| 5,308,506 | 5/1994 | McEwen et al. ....................... 210/789 |
| 5,354,483 | 10/1994 | Furse ..................................... 210/789 |
| 5,455,009 | 10/1995 | Vogler et al. .......................... 422/102 |

FOREIGN PATENT DOCUMENTS

0 341 586  11/1989  European Pat. Off. .

*Primary Examiner*—John Kim
*Attorney, Agent, or Firm*—William H. May; P. R. Harder; Steven G. Roeder

[57] ABSTRACT

A method for rapid separation of serum or plasma from cells in a whole blood sample uses a cylindrical sample tube having longitudinally-extending internal ribs. A separation gel and the sample are introduced into the tube, and the tube is axially centrifuged so as to form concentric shells of cells, gel, and serum or plasma. After centrifugation is stopped, the serum or plasma collects in the tube by gravity flow and the cells and gel remain affixed to the walls and ribs of the tube.

40 Claims, 5 Drawing Sheets

FIG. 11

AXIAL SPIN BLOOD SEPARATION SYSTEM AND METHOD

This is a continuation patent application of application Ser. No. 08/538,309 filed on Oct. 3, 1995, abandoned.

TECHNICAL FIELD

This invention relates to devices and methods for separating whole blood into its components.

BACKGROUND ART

Most clinical chemistry analysis requires a separated blood sample, and many analytical tests are performed on the liquid portion of the sample, i.e. plasma or, if the sample has not been treated with anticoagulants, serum. Separation of a usable sample of serum or plasma from whole blood is traditionally achieved by centrifuging blood collection tubes for five to fifteen minutes. Because blood separation time delays delivery of analytical results, devices and methods for rapid separations are highly desirable.

Rapid blood separation systems have been developed. For example, see U.S. Pat. Nos. 5,030,341 and 5,308,506 to McEwen et al. and U.S. Pat. Nos. 4,846,974 and 4,981,585 to Kelley et al. These systems require specialized blood collection or separation containers and internal separation elements, in addition to dedicated instruments, which add a continuing burden to the overall cost of the system.

What is needed is a simple blood separation method and device which is easy to use, contributes to the low cost operations of the laboratory, and rapidly provides a separated blood sample.

DISCLOSURE OF THE INVENTION

The above object has been achieved with an improved blood separation tube and system, and a method for rapidly separating serum or plasma from cells in a whole blood sample. The tube contains a plurality of longitudinally-extending internal ribs along an inside wall. The separation system and process utilize a gel having a density intermediate to densities of the blood components which are to be separated, and separation occurs via axial centrifugation.

Specifically, the gel is introduced into the tube and axial centrifugation is performed, i.e. the tube is spun about its longitudinal axis. The axial centrifugation causes the gel to be distributed about the tube, along the inside wall of the tube and to settle mostly within channels between the ribs of the tube. This step allows the gel to be distributed evenly throughout the tube and contributes to quick, even separations. The sample is then introduced into the prepared tube and axial centrifugation is repeated. This axial centrifugation step causes concentric shells of cells, gel, and serum or plasma to form within the tube. Once the centrifugation is stopped, the serum or plasma collects in the tube by gravity flow. The combination of internal ribs and gel serves to retain the outermost shell, which comprises blood cells, away from the liquid portion of the sample. The serum or plasma may be easily collected from the central portion of the tube through the use of a simple probe or needle.

Since the starting sample comprises whole blood, the tube is preferably evacuated and capped after introduction of the gel into the tube and before axial centrifugation to distribute the gel. This facilitates the blood collection and separation within the tube. The evacuation, capping, and gel distribution spinning steps may be performed at the point of manufacture so that an end user need only insert the sample and perform the sample separation spin. The tube may be spun in an upright vertical, inverted, horizontal, or other position. If the tube is processed in an inverted position, the serum or plasma may be accessed from the tube with a relatively short probe through the tube cap. The outer diameter of the tube is preferably the same as that of a standard blood collection tube, so that the tube of the present invention may be applied to a hospital or laboratory environment in a seamless manner.

Axial spinning allows rapid processing of samples, as the distance the cells must travel for separation is reduced significantly as compared to conventional centrifugation. Additionally, each sample may be processed as it arrives in the laboratory, rather than suffering the delay of batch processing dictated by a conventional centrifuge. The internal ribs help retain the gel in the form of a concentric shell, so that it resists the pull of gravity once the spinning has stopped. It is preferred that the internal ribs have top edges that stop a short distance below the inserted tube cap to allow the gel and cells to distribute evenly into each channel between the ribs.

The present invention has the advantage of utilizing inexpensive, modified tubes, and standard blood separation gel. These elements are combined in a unique way to rapidly provide serum or plasma for laboratory analysis.

DETAILED DESCRIPTION OF THE DRAWINGS

BEST MODE FOR CARRYING OUT THE INVENTION

Figure 1:
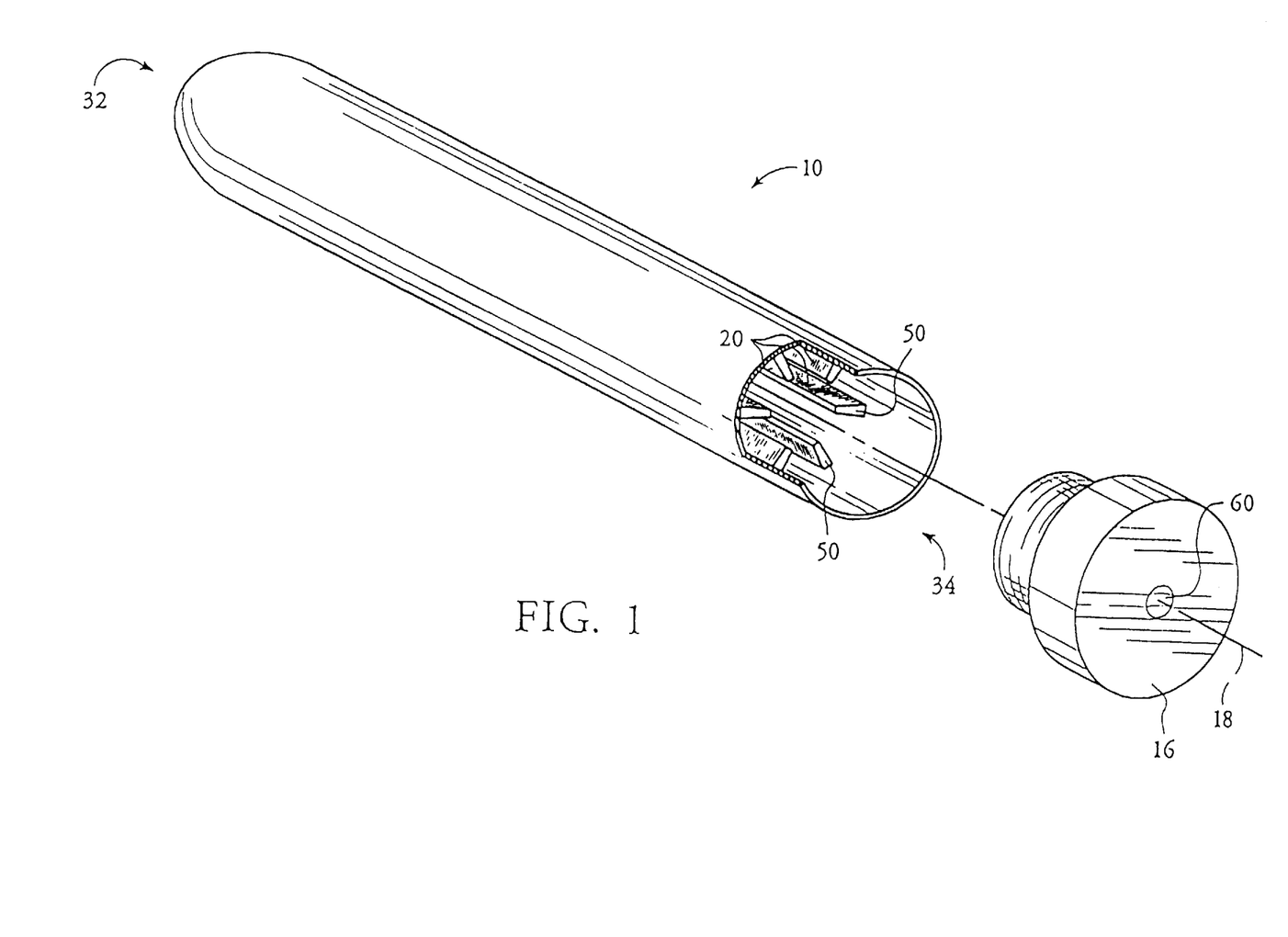
FIG. 1 is a perspective view of the sample tube of the present invention, with a partial cutaway showing internal ribs.

With reference to FIG. 1, a cylindrical sample tube 10 with an open top 34 is shown. Tube 10 is depicted in FIG. 1 with a partial cutaway of its side wall. The cutaway shows a plurality of longitudinally-extending internal ribs 20 within tube 10. The tube is single-chambered, and has an even annular cross-section, i.e. the internal ribs aside, it does not have a variable internal diameter. Cap 16, which is a standard tube cap, may be used in conjunction with the tube to contain the sample, and may include a small, covered bore 60 wherein a needle or other probe may easily pierce. The longitudinal axis 18 of the tube is also indicated. The internal ribs begin at the bottom 32 of the tube but preferably do not extend all the way to the open top 34 of the tube. When cap 16 is fully applied to the tube, the top edges 50 of the internal ribs 20 are spaced apart from cap 16.

Figure 2:
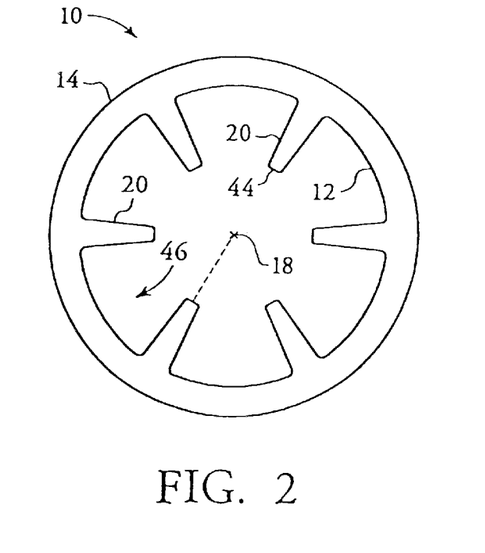
FIG. 2 is a cross sectional view of the tube, showing the positioning of the internal ribs.

FIG. 2 presents a cross section of tube 10, more clearly showing the outer wall 14 and inner wall 12 of the tube. FIG. 2 also shows the relative size and positioning of the internal ribs 20. The preferred embodiment of the present invention comprises six, equidistant internal ribs. Each rib begins at the inner wall of the tube and extends inwardly for approximately half the distance from the inner wall 12 to the longitudinal axis 18 of the tube, as indicated by the dashed line of FIG. 2. The peaks 44 of the ribs 20 and the channels 46 between the ribs are also shown. A different number of internal ribs and ribs of differing dimensions than shown may be useful, however, depending upon the relative volume of the sample and the gel. The tube 10 and ribs 20 preferably comprise a unitary piece formed of a plastic material.

Figure 3:
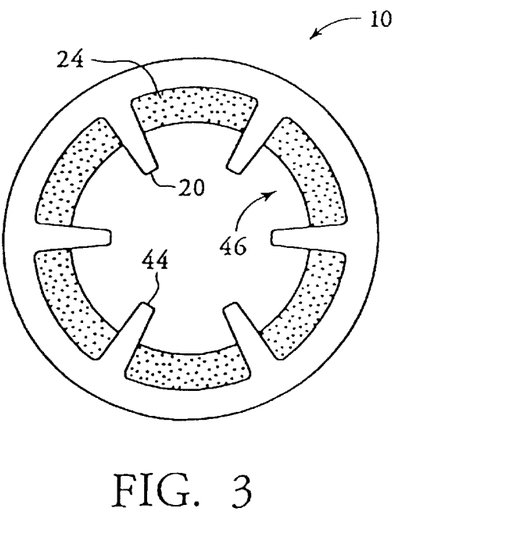
FIG. 3 is a cross sectional view of the tube, along axis 3—3 of FIG. 6, showing the preferred gel position.
Figure 6:
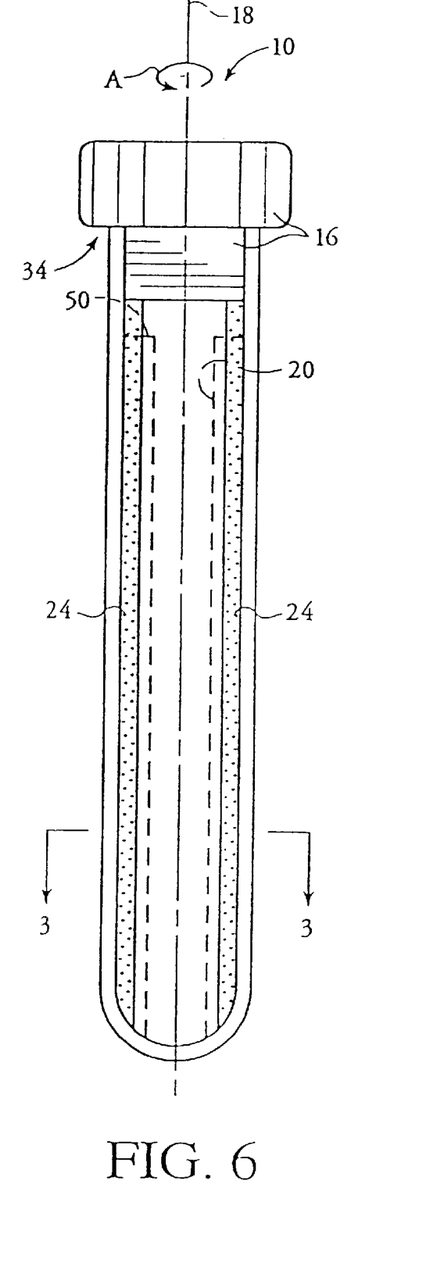
FIG. 6 is an elevational view of the tube containing gel which has been distributed by axial centrifugation, before addition of the sample.
Figure 8:
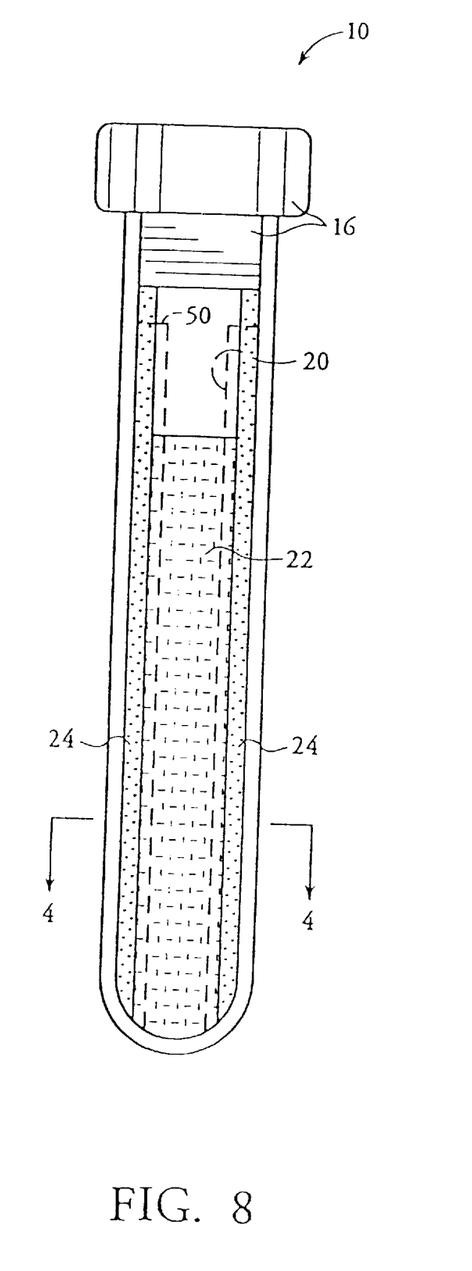
FIG. 8 is an elevational view of the tube of FIG. 6, with an addition of the unseparated sample to the distributed gel.

FIGS. 3 and 6 represent the first step in the method of the present invention wherein a separation gel 24 is introduced into tube 10 and axial centrifugation has taken place before introduction of the sample, i.e. the tube is spun about its longitudinal axis 18, e.g. in direction A. This preparation of the tube, and specifically the gel, before introduction of the sample allows the gel to disperse evenly and contributes to quick, clean separations. The use of gels in blood separations is well-known; e.g., see U.S. Pat. Nos. 4,386,003 and 3,852,194. FIG. 6 also shows that cap 16 has been applied to the open top 34 of tube 10 to contain the contents of the tube. With cap 16 in place, FIG. 6 clearly shows that the top edges 50 of ribs 20 are spaced apart from cap 16. Top edges 15 should not be spaced too far below cap 16, however, because the ribs 20 provide a support structure to the gel. A spacing of approximately 5% of the length of the tube is appropriate. The transverse cross sectional view of FIG. 3, presenting a view along axis 3—3 of FIG. 6, shows that gel 24 tends to collect in the channels 46 between the ribs of tube 10 when axially centrifuged. As stated above, this axial centrifugation to distribute the gel is preferably performed after the tube has been evacuated and capped. So that the contents of tube 10 may be more clearly illustrated, ribs 20 are depicted in FIGS. 6 and 8 with dashed lines. Additionally, the contents of the tube in elevational views 6 and 8–11 are in longitudinal cross-section so that the layers are easily visible.

Figure 7:
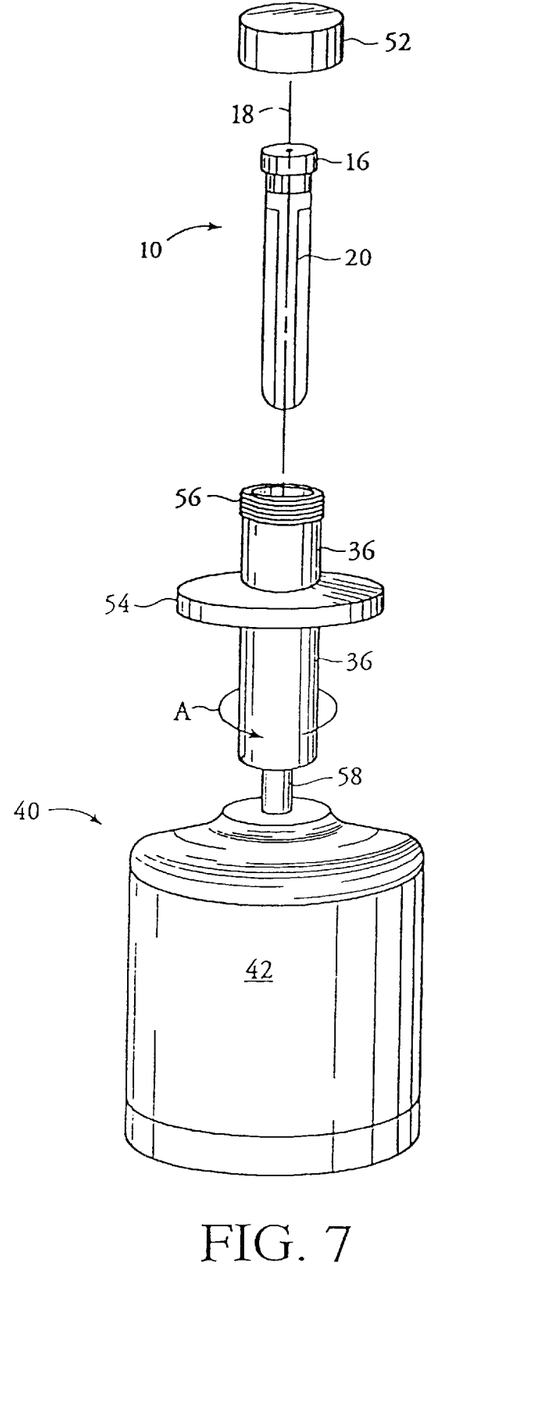
FIG. 7 is an exploded view of a means for axially centrifuging the tube.

FIG. 7 depicts an example of a means 40 for axially centrifuging or spinning the tube. In FIG. 7, a motor 42 has an attached spindle 58 to which is attached to a rotor 36. Rotor 36 is caused to rotate about its central axis, as in direction A, by motor 42. Tube 10 fits within rotor 36, with its longitudinal axis 18 generally coaxial with the central axis of the rotor. Threaded cap 52 may be mated with threading 56 of rotor 36 to secure tube 10 during high speed rotations. Alternatively, or in addition, motor 42 and rotor 36 may be contained within a housing having a lid to secure tube 10 within rotor 36. Rotor 36 may also have a stabilizing ring 54 disposed about its midsection.

Any means for axially centrifuging the sample may be used in the method of the present invention. Typically, a means for axially centrifuging a tube is intended to be part of a larger analytical instrument wherein the tube containing the sample is inserted into the instrument and centrifuged, and the serum or plasma is collected and transferred automatically, via a special probe, to another portion of the instrument where chemical tests are performed on the serum or plasma. Speeds in the range of 30,000–45,000 rpm (3000–7000 Gs) are generally sufficient to perform the separations described herein within one to two minutes. For completion of the separation, a spin time of three minutes or less in this range of speeds is suggested.

Figure 4:
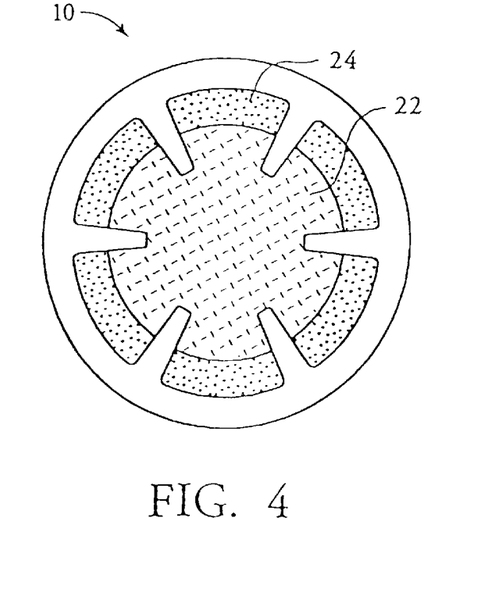
FIG. 4 is a cross sectional view of the tube, along axis 4—4 of FIG. 8, showing the gel and sample position before axial centrifugation of the sample.

FIG. 8 and its cross sectional view along axis 4—4, which is FIG. 4, show the prepared gel in tube 10 with the addition of the whole blood sample 22. Thus, after the gel has been placed in the tube and axially spun to distribute it, the next step is to introduce the sample into the tube. If the tube has been evacuated and capped, insertion of the sample may be performed through covered bore 60 of cap 16. In FIGS. 4 and 8, it can been seen that the blood sample 22 occupies not only the central portion of tube 10 but moves between ribs 20 to partially fill the channels 46.

Figure 9:
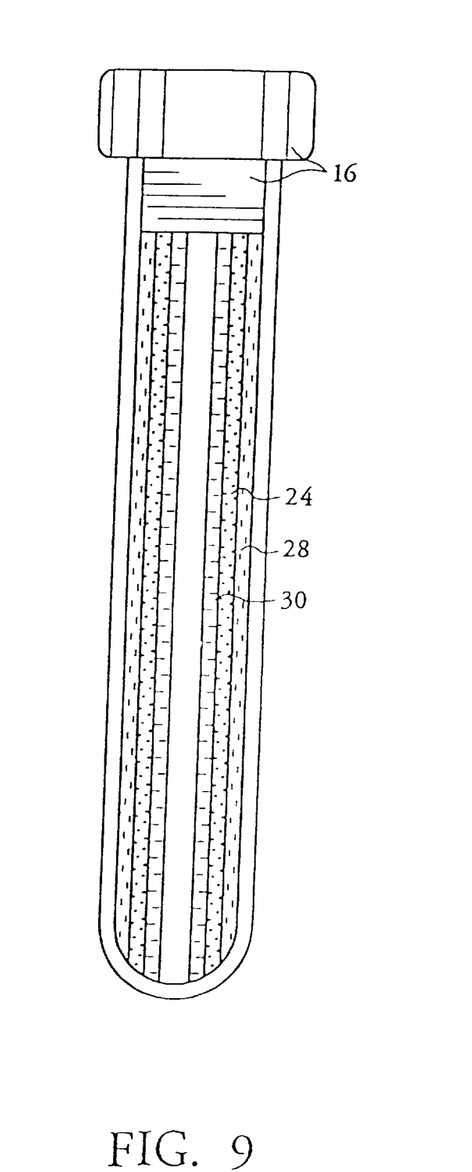
FIG. 9 is an elevational view of the tube showing the gel and sample during axial centrifugation.

FIG. 9 shows the contents of the tube during spinning. The axial centrifugation causes the tube contents to move radially toward the outer wall of tube 10, and to order themselves in generally concentric shells, according to their relative densities. Shell or layer 28 of FIG. 8 comprises blood cells. The blood cells have a density higher than that of the other contents of the tube, and thus travel through the gel and form the outermost shell 28. The gel 24 has a density intermediate to the densities of the blood components to be separated, in this case the blood cells and the serum or plasma. Therefore, the gel is lifted or displaced by the cells and forms a layer or shell 24 that is intermediate to that of the cells and the liquid portion of the sample. The innermost shell 30, which is visible in FIG. 9, comprises the liquid portion of the whole blood sample. The ribs 20 have been removed from FIGS. 9–11 in order to more clearly illustrate the shells.

The liquid portion 30 is serum or plasma depending upon whether the sample has been in contact with an anticoagulant, such as EDTA. Plasma is the result if the sample has been in contact with an anticoagulant. After centrifugation of such a sample, the liquid portion, i.e. plasma, contains clotting factors. Serum is collected, on the other hand, from a sample which has not been in contact with an anticoagulant. The blood sample is allowed to clot before processing, and, therefore, no clotting factors remain in the liquid portion. Collection of serum according to the method of the present invention may require slightly longer spin times or higher spin speeds than collection of plasma because the clots must travel through the gel for separation of the sample.

Figure 10:
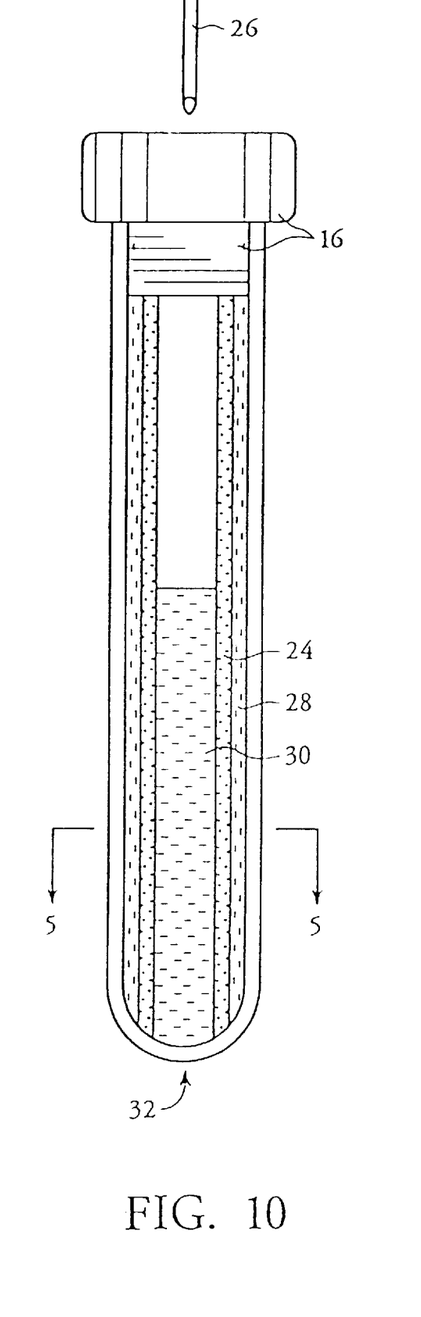
FIG. 10 is an elevational view of the tube showing the gel and sample after axial centrifugation has been terminated.

FIG. 10 shows tube 10 and its contents after axial spinning has been terminated. Since shell 30 of FIG. 9 contains the liquid portion of the sample, when spinning is stopped, this portion flows toward the bottom 32 of tube 10 by gravity flow. The gel portion 24 remains in its concentric shell form due to its viscosity and the internal ribs 20 of the tube which increase the surface area across which the gel may spread and adhere. The blood cells 28 are also retained as a concentric shell within the tube, because they are disposed between gel 24 and the tube wall. Thus, a separated sample having blood cells 28 removed from the serum or plasma portion 30 results from the use of tube 10, gel 24, and the method of the present invention. The serum or plasma portion 30 may easily be removed from the tube for further processing, as by inserting probe 26 into the center portion of the tube, away from the shells, and withdrawing the serum or plasma portion 30. Cap 16 may be removed to allow access to probe 26, or probe 26 may be inserted through cap 16.

Figure 5:
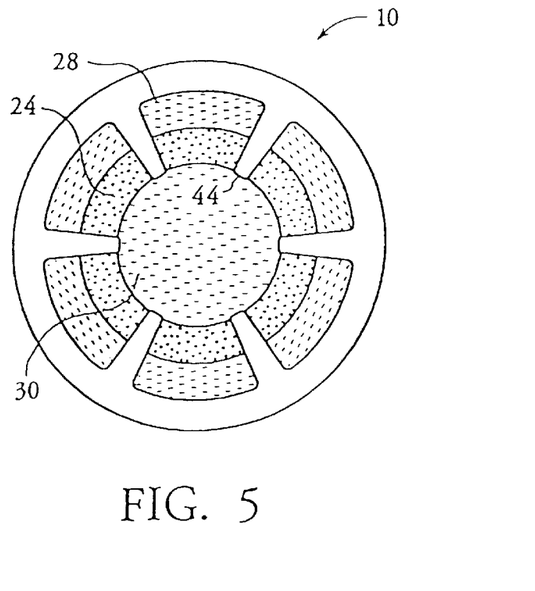
FIG. 5 is a cross sectional view of the tube, along axis 5—5 of FIG. 10, showing the separated sample according to the present invention.

FIG. 5 is a cross sectional view along axis 5—5 of FIG. 10. FIG. 5 affords another view of concentric shells formed by the axial centrifugation processing of the contents of tube 10. In FIG. 5, the end result of the migration of cells 28 through gel 24 can be seen. Meanwhile, the liquid portion 30 is left behind, on an axial side of the gel, and pools at the bottom of the tube. From FIG. 5, it can be seen that an amount of gel should be utilized which is sufficient to separate the sample, based on the amount of a typical sample, but insufficient to travel much beyond the peaks 44 of the internal ribs 20. If too much gel is used there will be little volume left for sample. Additionally, it may not adhere properly to the ribs of tube 10 and retain the blood cells 28. If too little is used, it is possible that a proper separation may not take place as the shell of gel may not be stiff enough to support itself when the spinning has ceased.

The general progression of the method of the present invention is made clear by viewing FIGS. 2, 3, 4 and 5 in succession. FIG. 2 depicts the empty tube with internal ribs. FIG. 3 shows the tube after the gel has been introduced and axial centrifugation has taken place, forming a first shell along an inside wall of tube 10. FIG. 4 shows the addition of the whole blood sample to the prepared tube. FIG. 5 shows the end result of the separation wherein the cells have migrated through the gel toward the outer walls of tube 10, and caused the displacement of gel 24. The axial centrifugation of whole blood is allowed to occur for a period of time sufficient to allow a majority of the blood cells to migrate through the gel and form a second shell between the first shell and the inside wall of tube 10. Serum or plasma 30 is left behind and, so, forms the innermost circle of FIG. 5.

Figure 11:
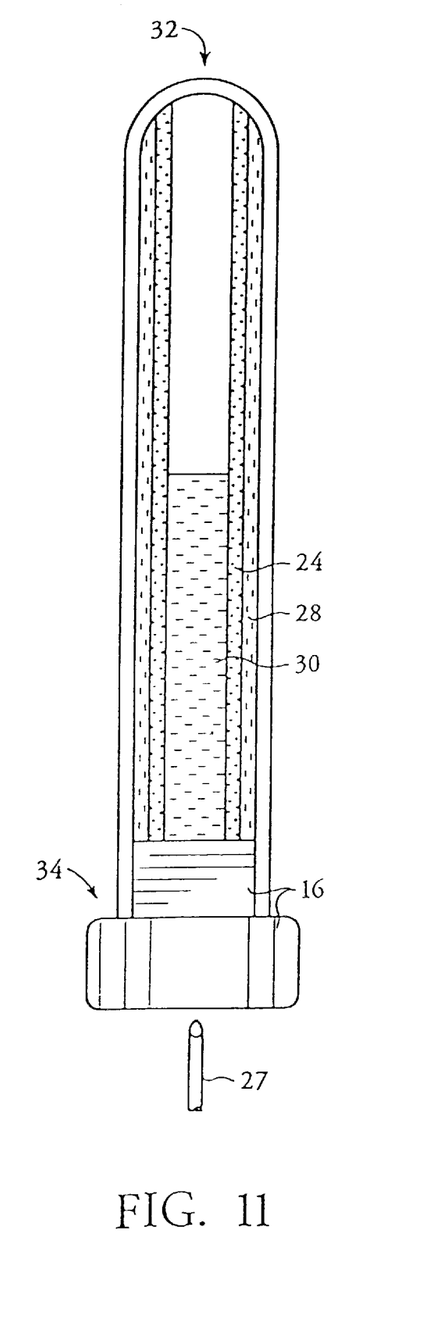
FIG. 11 is an elevational view of a tube showing inverted processing of the sample.

FIG. 11 represents an alternative, wherein the tube may be axially centrifuged while in an inverted position. Thus, the bottom of the tube 32 is shown at the top of FIG. 11 and the top of the tube 34, appropriately plugged by tube cap 16, is shown at the bottom of FIG. 11. Concentric shells 24, 28 and 30 form, as before, with liquid portion 30 flowing by gravity toward the top 34 of the tube. Processing in this inverted position has the advantage of allowing a shorter probe 27 to travel a short distance, through the tube cap 16, to access the serum or plasma portion 30 of the sample. Axial centrifugation may occur with tube 10 in a horizontal or other position, as well. Of course, the tube may also be inverted for access via the short probe after upright vertical processing. A vertical orientation of the tube, with the tube either upright, as in FIG. 9, or inverted, as in FIG. 11, is the preferred method, because the desired serum or plasma portion 30 will quickly pool and be easily accessible without further manipulation of the tube.

The device, system, and method of the present invention represent a simple, yet important, advance in blood processing. The modified tubes with internal ribs and the gel represent the only continuing expenses. The tubes themselves are preferably composed of a conventional plastic or other high impact, low cost, vacuum-tight material, e.g. a modified styrene copolymer such as butadiene-modified styrene, and may be manufactured inexpensively. A significant advantage provided by the invention is the short centrifugation times allowed by the axial spin design. The distance the cells must travel for separation is reduced from half the length of the tube in conventional processing to half the internal diameter of the tube in the axial spin process. Also, axial centrifugation has the advantage of allowing centrifugation of a single tube, as a sample comes into the laboratory, thereby eliminating the delay required with batch processing of multiple samples in tubes in conventional centrifuges.

We claim:

1. A method for separating serum or plasma from cells in a whole blood sample comprising:

introducing a separation gel into a cylindrical sample tube, the tube having a plurality of longitudinally-extending internal ribs, spinning the tube about its longitudinal axis so as to distribute the gel about the tube, introducing the sample into the tube, centrifuging the sample by spinning the tube about its longitudinal axis so as to form generally concentric shells of cells, gel, and serum or plasma, and stopping centrifugation and allowing the serum or plasma to collect by gravity flow.

2. The method of claim 1 further comprising:

evacuating and capping the tube after introducing the gel into the tube and before spinning the tube to distribute the gel and subsequently introducing the sample into the tube through a cap.

3. The method of claim 2 further comprising:

removing at least a portion of the collected serum or plasma from the tube by removing the cap from the tube and drawing the serum or plasma from a central portion of the tube.

4. The method of claim 2 further comprising:

removing at least a portion of the collected serum or plasma from the tube by drawing the serum or plasma through the cap from a central portion of the tube.

5. The method of claim 1 wherein centrifuging the sample by spinning the tube about its longitudinal axis further comprises centrifuging the sample while the tube is in an inverted position.

6. The method of claim 1 wherein centrifuging the sample by spinning the tube about its longitudinal axis further comprises spinning the tube at a speed in the range of 30,000 to 45,000 rpm.

7. The method of claim 6 wherein centrifuging the sample by spinning the tube about its longitudinal axis further comprises spinning the tube at a speed in the range of 30,000 to 45,000 rpm for three minutes or less.

8. The method of claim 1 wherein introducing the gel into the tube further comprises:

introducing an amount of gel sufficient to allow separation of the sample but insufficient to fill troughs between the internal ribs beyond peaks of the internal ribs.

9. A method for rapidly collecting serum or plasma comprising:

preparing a blood collection tube having longitudinally-extending internal ribs by inserting a separation gel into the tube and axially centrifuging the tube, causing the gel to form a first shell along an inside wall of the tube, inserting whole blood into the prepared tube, axially centrifuging the whole blood in the prepared tube for a period of time sufficient to allow a majority of cells of the blood to migrate through the gel, the cells forming a second shell positioned between the first shell and the inside wall of the tube, and the migration of the cells leaving serum or plasma on the axial side of the gel, stopping axial centrifugation, thereby allowing the serum or plasma on the axial side of the gel to pool via gravity flow, and removing at least a portion of the pooled serum or plasma from the tube.

10. The method of claim 9 further comprising:

evacuating and capping the tube before axially centrifuging the tube to cause the gel to form a first shell, wherein inserting whole blood into the prepared tube further comprises inserting the whole blood into the prepared tube through a cap.

11. The method of claim 10 wherein removing at least a portion of the pooled serum or plasma from the tube further comprises removing the portion through the cap while the tube is in an inverted position.

12. The method of claim 9 wherein axially centrifuging the whole blood in the prepared tube further comprises axially centrifuging the whole blood while the tube is in an inverted position.

13. The method of claim 9 wherein axially centrifuging the whole blood in the prepared tube further comprises axially centrifuging at a speed in the range of 30,000 to 45,000 rpm for three minutes or less.

14. A method for rapidly separating serum or plasma from cells in a whole blood sample by utilizing a blood collection tube having longitudinally-extending internal ribs and a separation gel distributed along the inside wall of the tube, the method comprising:

inserting the sample into the tube, axially centrifuging the sample at a speed and for a period of time sufficient to allow a majority of the cells to migrate through the gel to a position between the gel and the inside wall of the tube, leaving the serum or plasma on the axial side of the gel, stopping axial centrifugation, thereby allowing the serum or plasma on the axial side of the gel to pool via gravity flow, and removing at least a portion of the pooled serum or plasma from the tube.

15. The method of claim 14 wherein axially centrifuging the sample further comprises axially centrifuging at a speed in the range of 30,000 to 45,000 rpm.

16. The method of claim 14 wherein axially centrifuging the sample further comprises axially centrifuging for a period of time less than or equal to three minutes.

17. A blood separation system for separating serum or plasma from cells in a blood sample, the system comprising:

a cylindrical sample tube having a plurality of substantially, longitudinally-extending internal ribs, wherein each of the internal ribs cantilevers inwardly from proximate an inside wall of the tube;

a separation gel having a density intermediate to densities of blood components to be separated, the gel disposed within the tube along with the blood sample; and means for spinning the tube about its longitudinal axis so as to form substantially concentric shells of cells, gel, and serum or plasma.

18. The system of claim 17 wherein the internal ribs of the tube extend from proximate a bottom of the tube to proximate an open top of the tube.

19. The system of claim 17 wherein the internal ribs have top edges which are spaced-apart from a tube cap inserted fully into the top of the tube.

20. The system of claim 17 wherein the tube has an external diameter equivalent to an external diameter of a standard blood processing tube.

21. The system of claim 17 wherein the internal ribs of the tube are equidistant.

22. The system of claim 17 wherein each of the internal ribs of the tube extends inwardly to approximately half the distance from the inside wall of the tube to the longitudinal axis of the tube to support the shell of gel between the cells and the serum or plasma.

23. The system of claim 17 wherein the plurality of longitudinally-extending internal ribs of the tube is equal to six internal ribs.

24. The system of claim 17 wherein the tube and ribs are comprised of a modified styrene copolymer.

25. In a cylindrical blood separation tube designed for separating serum or plasma from cells in a blood sample during centrifugation, the improvement comprising:

a substantially concentric shell of a separation gel positioned within the tube; and a plurality of substantially, longitudinally-extending internal ribs along an inside wall of the tube which retain the gel in the substantially concentric shell, wherein each of the internal ribs cantilevers inwardly from proximate an inside wall of the tube to support the shell of gel between the cells and the serum or plasma upon axial centrifugation.

26. The improvement of claim 25 wherein the internal ribs have top edges which are spaced-apart from a tube cap inserted fully into the top of the tube.

27. The improvement of claim 25 wherein the internal ribs are equidistant.

28. The improvement of claim 25 wherein the plurality of longitudinally-extending internal ribs is equal to six internal ribs.

29. The improvement of claim 25 wherein the internal ribs and the tube further comprise a single unitary piece.

30. A blood separating device for separating serum or plasma from cells in a blood sample, the device comprising a sample tube having a longitudinal axis and a plurality of substantially longitudinally extending internal ribs attached to the sample tube; and a separation gel distributed within the tube and forming a shell of gel which is substantially coaxial with the longitudinal axis of the tube, the shell of gel being supported by the internal ribs.

31. The blood separating device of claim 34 wherein at least one of the internal ribs substantially cantilevers inwardly from proximate an inside wall of the sample tube.

32. The blood separating device of claim 30 wherein each of the ribs substantially cantilevers inwardly from proximate an inside wall of the tube.

33. The blood separating device of claim 30 wherein the sample tube is substantially tubular shaped.

34. The blood separating device of claim 30 including means for spinning the sample tube about its longitudinal axis so as to form the shell of gel.

35. A method for separating serum or plasma from cells in a blood sample with a separation gel, the method comprising the steps of:

introducing the separation gel and the sample into a sample tube, the sample tube having a plurality of substantially longitudinally extending internal ribs attached to the sample tube to support the separation gel; and spinning the sample tube to form substantially concentric shells of cells and gel.

36. The method of claim 35 including the step of providing a sample tube prior to the step of introducing the separation gel and the sample, the sample tube having at least one of the internal ribs substantially cantilevering inwardly from proximate an inside wall of the tube.

37. The method of claim 35 wherein the step of introducing the sample and the separation gel includes the steps of introducing the separation gel into the sample tube, spinning the sample tube substantially about a longitudinal axis of the sample tube so as to distribute the gel about the sample tube, and introducing the sample into the sample tube.

38. A method for manufacturing a blood separation device comprising the steps of:

provanding a sample tube having a longitudinal axis and a plurality of substantially longitudinally extending internal ribs attached to the sample tube; and distributing a separation gel within the tube to form a shell of gel within the tube which is substantially coaxial with the longitudinal axis.

39. The method of claim 38 wherein the step of distributing the separation gel includes the step of rotating the sample tube substantially about the longitudinal axis of the sample tube.

40. The method of claim 38 wherein the step of providing a sample tube includes providing a sample tube wherein at least one of the internal ribs substantially cantilevers inward from proximate an inside wall of the tube.

* * * * *